US00PP29964P3

(12) United States Plant Patent
Meulenbroek

(10) Patent No.: US PP29,964 P3
(45) Date of Patent: Dec. 11, 2018

(54) STRAWBERRY PLANT NAMED 'ALLEGRO'

(50) Latin Name: *Fragaria x ananassa*
Varietal Denomination: Allegro

(71) Applicant: Egbertus Joseph Meulenbroek, Zetten (NL)

(72) Inventor: Egbertus Joseph Meulenbroek, Zetten (NL)

(73) Assignee: Fresh Forward Holding B.V., Ecken Wiel (NL)

( * ) Notice: Subject to any disclaimer, the term of this patent is extended or adjusted under 35 U.S.C. 154(b) by 1 day.

(21) Appl. No.: 15/530,478

(22) Filed: Jan. 20, 2017

(65) Prior Publication Data

US 2018/0213697 P1 Jul. 26, 2018

(51) Int. Cl.
*A01H 5/08* (2018.01)
*A01H 6/74* (2018.01)

(52) U.S. Cl.
USPC ..... Plt./208
CPC ..... *A01H 6/7409* (2018.05)

(58) Field of Classification Search
USPC ..... Plt./208, 209
See application file for complete search history.

(56) References Cited

PUBLICATIONS

UPOV-PLUTO:Plant Variety Database—citation for 'Allegro'.*

* cited by examiner

*Primary Examiner* — Susan McCormick Ewoldt
(74) *Attorney, Agent, or Firm* — C. A. Whealy

(57) ABSTRACT

A new and distinct cultivar of Strawberry plant named 'Allegro', characterized by its compact and upright plant habit; moderately vigorous to vigorous growth habit; uniform and early fruit ripening; medium-sized ovoid fruits that are moderately glossy and red in color; pleasant fruit aroma and taste; excellent fruit postharvest longevity; and moderate resistance to *Phytophthora cactorum.*

2 Drawing Sheets

Botanical designation: *Fragaria* x *ananassa.*
Cultivar denomination: 'ALLEGRO'.

BACKGROUND OF THE INVENTION

The present Invention relates to a new and distinct cultivar of Strawberry plant, botanically known as *Fragaria* x *ananassa* and hereinafter referred to by the name 'Allegro'.

The new Strawberry plant is a product of a planned breeding program conducted by the Inventor in Eck en Wiel, The Netherlands. The objective of the breeding program was to develop new early-ripening Strawberry plants with good fruit quality, ease of harvesting, good postharvest longevity and resistance to pathogens.

The new Strawberry plant originated from a cross-pollination by the Inventor during the spring of 2008 in Eck en Wiel, The Netherlands of a proprietary selection of *Fragaria* x *ananassa* identified as code number E2003-097, not patented, as the female, or seed, parent with a proprietary selection of *Fragaria* x *ananassa* identified as code number E2006-492, not patented, as the male, or pollen, parent. The new Strawberry plant was discovered and selected by the Inventor as a single plant from within the progeny of the stated cross-pollination in a controlled environment in Eck en Wiel, The Netherlands during the summer of 2010.

Asexual reproduction of the new Strawberry plant by runner cuttings in a controlled environment at Eck en Wiel, The Netherlands since the autumn of 2010, has shown that the unique features of this new Strawberry plant are stable and reproduced true to type in successive generations of asexual reproduction.

SUMMARY OF THE INVENTION

Plants of the new Strawberry have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Allegro'. These characteristics in combination distinguish 'Allegro' as a new and distinct Strawberry plant:

1. Compact and upright plant habit.
2. Moderately vigorous to vigorous growth habit.
3. Uniform and early fruit ripening.
4. Medium-sized ovoid fruits that are moderately glossy and red in color.
5. Pleasant fruit aroma and taste.
6. Excellent fruit postharvest longevity.
7. Moderately resistant to *Phytophthora cactorum.*

Plants of the new Strawberry differ primarily from plants of the female parent selection in the following characteristics:

1. Plants of the new Strawberry are more upright than and not as flat as plants of the female parent selection.
2. Fruits of plants of the new Strawberry are ovoid in shape whereas fruits of plants of the female parent selection are conical in shape.

Plants of the new Strawberry differ primarily from plants of the male parent selection in the following characteristics:

1. Plants of the new Strawberry are more vigorous than plants of the male parent selection.
2. Leaves of plants of the new Strawberry are darker green in color than leaves of plants of the male parent selection.

Plants of the new Strawberry can be compared to plants of *Fragaria L.* 'Sonata', disclosed in U.S. Plant Pat. No. 18,000. In side-by-side comparisons, plants of the new Strawberry differ primarily from plants of 'Sonata' in the following characteristics:

1. Plants of the new Strawberry are more upright than and not as flat as plants of 'Sonata'.
2. Plants of the new Strawberry are more vigorous than plants of 'Sonata'.
3. Plants of the new Strawberry have longer leaves with typically longer petioles than plants of 'Sonata'.
4. Plants of the new Strawberry flower and fruit earlier than plants of 'Sonata'.
5. Fruits of plants of the new Strawberry are darker in color than fruits of plants of 'Sonata'.
6. Fruits of plants of the new Strawberry are heavier and firmer than fruits of plants of 'Sonata'.

Plants of the new Strawberry can also be compared to plants of *Fragaria L.* 'Honeoye', not patented. In side-by-side comparisons, plants of the new Strawberry differ primarily from plants of 'Honeoye' in the following characteristics:

1. Fruits of plants of the new Strawberry are lighter in color than fruits of plants of 'Honeoye'.
2. Achenes of plants of the new Strawberry are level with the fruit surface whereas achenes of plants of 'Honeoye' are positioned below the fruit surface.

BRIEF DESCRIPTION OF THE PHOTOGRAPHS

The accompanying colored photographs illustrate the overall appearance of the new Strawberry plant showing the colors as true as it is reasonably possible to obtain in colored reproductions of this type. Colors in the photographs may differ slightly from the color values cited in the detailed botanical description which accurately describe the colors of the new Strawberry plant.

The photograph on the first sheet is a top perspective view of a typical plant of 'Allegro'.

The photograph on the second sheet is a close-up view of typical leaves, developing fruits and developed fruits of a typical plant of 'Allegro'.

DETAILED BOTANICAL DESCRIPTION

The aforementioned photographs, following observations and measurements describe plants grown in ground beds during the spring and summer in a glass-covered greenhouse in Elst, Gelderland, The Netherlands and under cultural practices typical of commercial Strawberry production. During the production of the plants, day temperatures ranged from 15° C. to 25° C. and night temperatures ranged from 7° C. to 14° C. Plants were one year old when the photographs and description were taken. In the following description, color references are made to The Royal Horticultural Society Colour Chart, 2001 Edition, except where general terms of ordinary dictionary significance are used.

Botanical classification: *Fragaria* x *ananassa* 'Allegro'.

Parentage:

*Female, or seed, parent.*—Proprietary selection of *Fragaria* x *ananassa* identified as code name E2003-097, not patented.

*Male, or pollen, parent.*—Proprietary selection of *Fragaria* x *ananassa* identified as code name E2006-492, not patented.

Propagation:

*Type.*—By runner cuttings.

*Time to initiate roots, summer.*—About one to four days at soil temperatures about 15° C. and ambient temperatures about 17° C.

*Time to produce a rooted young plant, summer.*—About two weeks at soil temperatures ranging from 18° to 20° C. and ambient temperatures about 17° C.

*Root description.*—Medium in thickness, fibrous; typically cream white to white in color, actual color of the roots is dependent on substrate composition, water quality, fertilizer type and formulation, substrate temperature and physiological age of roots.

*Rooting habit.*—Moderately freely branching; medium density.

Plant description:

*Plant and growth habit.*—Perennial; compact and upright plant habit; leaves basal; moderately vigorous to vigorous growth habit; moderate growth rate.

*Plant height.*—About 25 to 35 cm.

*Plant diameter.*—About 35 to 40 cm.

*Quantity of stolons per plant.*—Above average, about 90.

Leaf description:

*Arrangement.*—Basal rosette; compound with typically three or four leaflets per leaf.

*Leaflet length.*—About 10 to 13 cm.

*Leaflet width.*—About 7 to 10 cm.

*Leaflet shape.*—Broadly ovate.

*Leaflet apex.*—Obtuse to acute.

*Leaflet base.*—Obtuse to rounded.

*Leaflet margin.*—Serrate to lobed.

*Leaflet texture, upper surface.*—Pubescent.

*Leaflet texture, lower surface.*—Pubescent, rough.

*Leaflet venation.*—Pinnate.

*Leaflet color.*—Developing leaflets, upper surface: Close to 137A. Developing leaflets, lower surface: Close to 138A. Fully expanded leaflets, upper surface: Close to between 137A and 139A; venation, close to 144C. Fully expanded leaflets, lower surface: Close to 138A; venation, close to 144C.

*Petioles.*—Length: About 15 to 35 cm. Diameter: About 2 to 4 mm. Texture, upper and lower surfaces: Pubescent. Color, upper and lower surfaces: Close to 145A.

Flower description:

*Flower form and flowering habit.*—Rotate flowers arranged singly at lateral apices; flowers held mostly upright and below the foliar plane.

*Fragrance.*—None detected.

*Natural flowering season.*—Plants flower in late April to early May in The Netherlands.

*Flower diameter.*—About 2 to 3 cm.

*Flower depth (height).*—About 3 mm to 5 mm.

*Petals.*—Arrangement: Single whorl of five or six petals; petals not imbricate. Length: About 6 mm to 9 mm. Width: About 7 mm to 10 mm. Shape: Round to broadly ovate. Apex: Rounded. Base: Attenuate. Margin: Entire. Texture, upper and lower surfaces: Smooth, glabrous; satiny. Color: When opening and fully opened, upper surface: Close to 155D. When opening and fully opened, lower surface: Close to 155D.

*Sepals*.—Arrangement and calyx description: Twelve to 14 sepals arranged in about two whorls; calyx, star-shaped; sepals are orientated upwards from the fruit. Length: About 1 cm to 1.5 cm. Width: About 2 mm to 5 mm. Shape: Lanceolate to ovate. Apex: Acute. Base: Fused. Margin: Entire. Texture, upper and lower surfaces: Pubescent. Color, upper and lower surfaces: Close to 137A.

*Peduncles*.—Length: About 7 cm to 10 cm. Diameter: About 1 mm to 2 mm. Strength: Strong. Texture: Pubescent. Color: Close to 144B.

*Pedicels*.—Length: About 3 cm to 10 cm. Diameter: About 1 mm to 3 mm. Strength: Strong. Texture: Pubescent. Color: Close to 144B.

*Reproductive organs*.—Stamens: Quantity per flower: About 25 to 30. Anther length: About 2 mm. Anther shape: Lanceolate to elliptic. Anther color: Close to 14B. Pollen amount: Abundant. Pollen color: Close to 15C. Pistils: Quantity per flower: About 30. Pistil length: About 1 mm to 2 mm. Stigma shape: Rounded. Stigma color: Close to 5A. Fruiting truss: Length: About 3.8 cm. Diameter: About 3.7 cm. Color: Close to 34A. Quantity of fruits per truss: About seven to twelve. Fruits: Quantity per plant: About 25 to 35. Natural fruiting season: Relatively early and long fruiting season, plants develop fruit from early June until early July in The Netherlands. Postharvest longevity: About ten days at 7° C. Length: About 2 cm to 5 cm. Diameter: About 2 cm to 3.5 cm. Shape: Ovoid. Fruit weight per fruit, first quality: About 18 g. Fruit weight per plant, first quality: About 420 g. Firmness: Firm. Fragrance, taste: Pleasant; good balance between sweetness and acidity. Luster: Uniformly moderately glossy. Surface unevenness: Smooth. Color, surface: Close to 34A. Color, flesh: Close to 33B. Seed density: Medium; about eleven seeds per $cm^2$. Achene position: Level with fruit surface. Achene color: Close to 1A.

Disease and pest resistance: Plants of the new Strawberry have been observed to be moderately resistant to *Phytophthora cactorum*. Plants of the new Strawberry have not been observed to be resistant to pests and other pathogens common to Strawberry plants.

It is claimed:

1. A new and distinct Strawberry plant named 'Allegro' as illustrated and described.

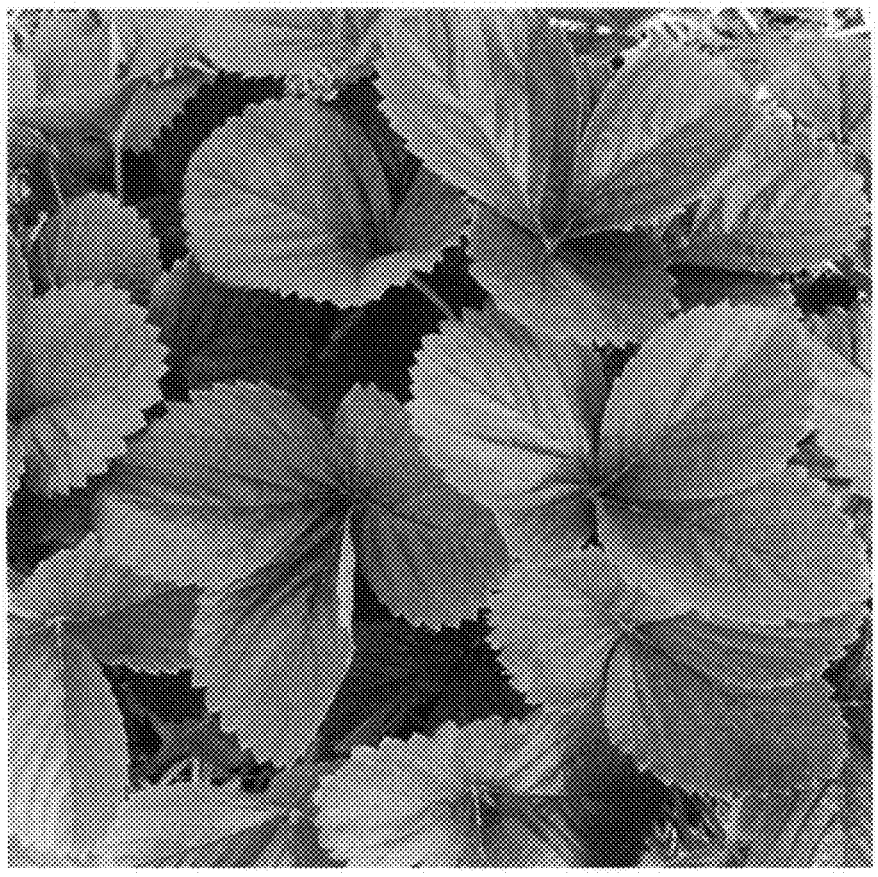

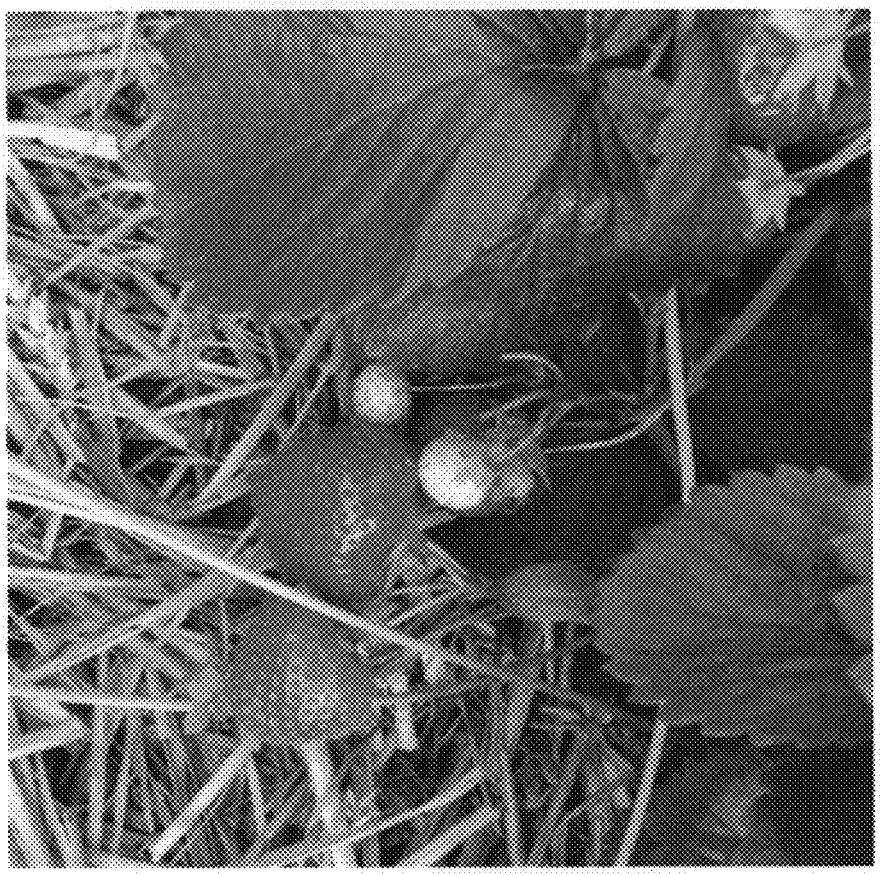

* * * * *